United States Patent
Yang et al.

(10) Patent No.: US 9,630,903 B2
(45) Date of Patent: Apr. 25, 2017

(54) PROCESS FOR PREPARING AND SEPARATING MONODISPERSE POLYETHYLENE GLYCOL

(71) Applicants: NANJING CARBONDE TECH CO., LTD., Nanjing, Jiangsu (CN); OPEGCHEM COMPANY, INC., Rancho Cucamonga, CA (US)

(72) Inventors: Zhuhong Yang, Nanjing (CN); YouQin Wu, Nanjing (CN)

(73) Assignees: Nanjing Carbonde Tech. Co., Ltd., Nanjing (CN); Opegchem Company, Inc., Rancho Cucamonga, CA (US)

( * ) Notice: Subject to any disclaimer, the term of this patent is extended or adjusted under 35 U.S.C. 154(b) by 0 days.

(21) Appl. No.: 14/842,027

(22) Filed: Sep. 1, 2015

(65) Prior Publication Data

US 2016/0075624 A1    Mar. 17, 2016

(30) Foreign Application Priority Data

Sep. 17, 2014    (CN) .......................... 2014 1 0476873

(51) Int. Cl.
| | | |
|---|---|---|
| *C07C 41/18* | (2006.01) | |
| *C07C 41/36* | (2006.01) | |
| *C07C 67/14* | (2006.01) | |
| *C07C 67/56* | (2006.01) | |
| *C07C 41/26* | (2006.01) | |
| *C07C 41/44* | (2006.01) | |
| *C08G 65/00* | (2006.01) | |

(52) U.S. Cl.
CPC .............. *C07C 67/14* (2013.01); *C07C 41/26* (2013.01); *C07C 41/44* (2013.01); *C07C 67/56* (2013.01); *C08G 65/00* (2013.01)

(58) Field of Classification Search
None
See application file for complete search history.

(56) References Cited

U.S. PATENT DOCUMENTS

2005/0054816 A1*    3/2005    McManus ........ A61K 47/48215
528/425

OTHER PUBLICATIONS

Faust, Chromatography, Modern Chemical Techniques: An Essential Reference for Students and Teachers, Royal Society of Chemistry, Jan. 1997, pp. 116-159).*

* cited by examiner

*Primary Examiner* — Rosalynd Keys
(74) *Attorney, Agent, or Firm* — Oliff PLC

(57) ABSTRACT

A process for preparing and separating a monodisperse polyethylene glycol, including: dissolving a starting material of polyethylene glycol into an organic solvent for reaction with a compound represented by general formula I under catalytic action of an alkaline substance, to prepare a mixture of derivatives of polyethylene glycol having different polarities; separating the mixture of derivatives of polyethylene glycol by means of silica gel column chromatography, to obtain a monodisperse derivative of polyethylene glycol; and hydrolyzing the derivative of polyethylene glycol to obtain a monodisperse polyethylene glycol. The starting material is industrially prepared polyethylene glycol with a wide source and low cost, which provides a guarantee for popularization and application of a monodisperse polyethylene glycol product.

13 Claims, 2 Drawing Sheets

PROCESS FOR PREPARING AND SEPARATING MONODISPERSE POLYETHYLENE GLYCOL

BACKGROUND

Technical Field

The present invention relates to the field of biomaterials, life science and medicines, and in particular, to a monodisperse polyethylene glycol preparation and separation process, to obtain a monodisperse polyethylene glycol.

Related Art

Polyethylene glycol has an excellent biocompatibility, and functionalized polyethylene glycol can modify a bioactive molecule. After being grafted to a bioactive molecule such as a drug molecule, water solubility, biocompatibility and stability of functionalized polyethylene glycol may be improved, and toxicity thereof is reduced. The polyethylene glycol is an important intermediate for achieving delivery and controlled release of a drug. However, industrial grade polyethylene glycol is generally prepared by stepwise addition polymerization of ethylene oxide and water or ethylene glycol. The product is a mixture of polyethylene glycols with different but similar molecular weights, similar molecular structures, and wide molecular weight distribution, and cannot be separated by using a conventional separation method nor directly used for drug modification. An indicator for evaluating the range of molecular weight distribution thereof is represented by a polydispersity index. The polydispersity index is an important concept in the polymer science, and sometimes called molecular weight distribution coefficient, dispersity and the like. The polydispersity index is defined as a ratio of weight-average molecular weight to number-average molecular weight, and represented by Mw/Mn.

At present, polyethylene glycol used as a carrier of a drug or bioactive molecule is separated by using a preparative high performance liquid chromatography column. The column efficiency is over 10,000 theoretical plates, and the required polydispersity index is less than 1.1. Currently, polyethylene glycol has a minimum polydispersity index of 1.04. However, preparation conditions according to the method are rigorous, and requirements for purity of reagents and solvents are extremely high. As a result, large-scale production is not easily achieved. In addition, the product is still a mixture of polyethylene glycols with different molecular weights, and thus, it is difficult to ensure reproducibility of drug efficiency and performance of a bioactive molecule. Therefore, high purity monodisperse polyethylene glycol is a focus of research and application of a bioactive molecule such as a drug molecule. According to Chen et al., monodisperse polyethylene glycol was prepared by synthesis of triphenylmethyl polyethylene glycol and polyethylene glycol p-toluenesulfonate. In the method, the synthetic route requires a long duration, and the starting material has very similar properties with the by-products and is difficultly removed from the products. Davis et al. reacted a small-molecule polyethylene glycol with a bifunctionalized polyethylene glycol or a functionalized polyethylene glycol intermediate having a single protecting group, to achieve growth of a polyethylene glycol chain. The method has main disadvantages as follows: an expensive palladium-carbon catalyst needs to be used for hydrogenation and deprotection under high pressure, and in addition, due to a functionalized polyethylene glycol being used as a starting material, there is a very great limit to the source of the starting material, which inevitably leads to an improved cost. As a result, the price is generally very high.

SUMMARY

An objective of the present invention is to prepare a monodisperse polyethylene glycol by the following process: using industrial grade polyethylene glycol that is obtained by stepwise addition polymerization of ethylene oxide and water or ethylene glycol as a starting material, and performing functional group modification thereon, to transform a mixture of polyethylene glycols with similar molecular weights and structures to a mixture of derivatives of polyethylene glycol having different polarities; then utilizing polarity differences of the derivatives of polyethylene glycol, to separate the mixture by using silica gel column chromatography; collecting components with different polarities, to obtain a monodisperse derivative of polyethylene glycol; and then hydrolyzing the derivative of polyethylene glycol under an acid or alkaline environment.

The objective of the present invention can be achieved by the following approaches:

A process for preparing and separating a monodisperse polyethylene glycol is provided, including: dissolving a starting material of polyethylene glycol into an organic solvent for reaction with a compound represented by general formula I under catalytic action of an alkaline substance, to prepare a mixture of derivatives of polyethylene glycol having different polarities; separating the mixture of derivatives of polyethylene glycol by means of silica gel column chromatography, to obtain a monodisperse derivative of polyethylene glycol; and hydrolyzing the derivative of polyethylene glycol to obtain a monodisperse polyethylene glycol, where, general formula I is as follows:

where: R is selected from a $C_1$-$C_4$ alkyl and aryl; and B is selected from a chloride ion, a bromide ion, an iodide ion, sulfydryl, sulfonyl, an isocyanate group, and an isocyanurate group.

Preferably, the $C_1$-$C_4$ alkyl is selected from methyl, ethyl, n-propyl, isopropyl, 1-butyl, 2-butyl, and isobutyl; and the aryl is selected from phenyl, 2-methylphenyl, 4-methylphenyl, benzyl, 2-methylbenzyl, 4-methylbenzyl, 4-tosyl, and triphenylmethyl.

The compound represented by general formula I is preferably isobutyl chloride, triphenylmethyl chloride, 4-methylbenzyl bromide, or 4-methylbenzenesulfonyl chloride.

The starting material of polyethylene glycol has general formula of:

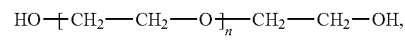

where: n=3 to 50, and a polydispersity index thereof is greater than 1.1.

The derivatives of polyethylene glycol with different polarities have general formula of:

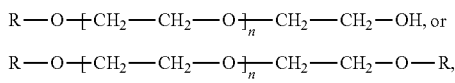

where: n=3 to 50.

The monodisperse polyethylene glycol has a polydispersity index of 1 to 1.03, preferably 1 to 1.005.

A molar ratio of the starting material of polyethylene glycol to a compound represented by general formula I is 2:1 to 100:1, preferably 4:1 to 20:1.

A molar ratio of the starting material of polyethylene glycol to an alkaline substance is 1:1 to 20:1, preferably 2:1 to 7:1.

The reaction temperature of the starting material of polyethylene glycol and a compound represented by general formula I is −20° C. to 150° C., preferably 0° C. to 60° C.; and the reaction duration thereof is 3 h to 72 h, preferably 8 h to 72 h.

The organic solvent is at least one of dichloromethane, trichloromethane, benzene, toluene, dimethylformamide, dimethyl sulfoxide, tetrahydrofuran and 1,4-dioxane, preferably tetrahydrofuran and 1,4-dioxane.

The alkaline substance is at least one of an alkali metal, an alkaline-earth metal, and a corresponding oxide, hydroxide, and hydride thereof, preferably sodium metal, sodium hydroxide and sodium hydride.

During the process of silica gel column chromatography, an eluent is a mixture of two of formamide, acetonitrile, methanol, ethanol, propanol, acetone, dioxane, tetrahydrofuran, methyl ethyl ketone, n-butanol, ethyl acetate, diethyl ether, isopropyl ether, dichloromethane, chloroform, benzene, tetrachloromethane, carbon disulfide, cyclohexane, n-hexane and petroleum ether, preferably a mixed solvent (P/E) of ethyl acetate and petroleum ether or a mixed solvent (D/M) of dichloromethane and methanol. Further, the eluent is preferably a mixed solvent (P/E=1:1) of ethyl acetate and petroleum ether with a volume ratio of 1:1, a mixed solvent (P/E=3:1) of ethyl acetate and petroleum ether with a volume ratio of 3:1, or a mixed solvent (D/M=10:1) of dichloromethane and methanol with a volume ratio of 10:1.

The derivative of polyethylene glycol is hydrolyzed under an acid or alkaline environment to obtain a monodisperse polyethylene glycol.

Compared with the prior art, the present invention has the following advantages:

The starting material used in the present invention is industrially prepared polyethylene glycol with a wide source and low cost, which provides a guarantee for popularization and application of a monodisperse polyethylene glycol product.

The separation method used in the present invention is silica gel column chromatography that is commonly known in the art, which features a simple process with less than 100 theoretical plates and a low separation cost, and is generally used for experiments, preparation and separation in corresponding fields.

The monodisperse polyethylene glycol product prepared by using the method of the present invention has a unique molecular weight and high purity, and after being grafted to a bioactive molecule such as a drug molecule, the stability and reproducibility thereof is high.

DETAILED DESCRIPTION

The following describes the present invention with reference to specific embodiments, but the present invention is not limited thereto.

Embodiment 1

40 g (0.1 mol) of polyethylene glycol PEG-400 was taken as a starting material, which has a molecular weight distribution range of 380 to 420 and a distribution index of 1.15. The polyethylene glycol was dissolved in 1,000 ml of 1,4-dioxane and cooled to 0° C. Then, to the resulting solution, 2 g (0.025 mol) of 50% (mass percentage content, the same below) sodium hydroxide solution was added dropwise and further stirred for 2 h. 2.3 g (0.025 mol) of isobutyl chloride was then added for reaction at a temperature of 0° C. over 24 h. 300 ml of saturated ammonium chloride solution was added to the reaction liquid and then stirred for stratification. An organic phase was washed with saturated aqueous solution of sodium chloride to neutral, and after the solvent was removed by means of vacuum concentration, a mixed sample of 8.0 g of polyethylene glycol mono(isobutyl) ester was obtained. To the above sample, 12 g of silica gel and 50 ml of ethyl acetate were added, evenly dispersed and dried to prepare a silica gel sample. 200 g of silica gel was added into a glass chromatography column with a diameter of 80 mm, and vibrated to become dense. Then, the above silica gel sample and a small amount of anhydrous sodium sulfate were added into the glass chromatography column, to prevent surface disturbance of the silica gel sample. After a silica gel column for chromatography was formed, a mixed solvent (P/E=1:1) of ethyl acetate and petroleum ether with a volume ratio of 1:1 was slowly added as an eluent continuously. Samples of different components were collected according to different polarities, and after the eluent was removed, derivatives of polyethylene glycol with a pure component were obtained. Then, 100 ml of 5% sodium hydroxide solution was separately added into the derivatives of polyethylene glycol, stirred at 50° C. and hydrolyzed for 8 h. After being cooled, the derivatives of polyethylene glycol were separately extracted with 100 ml of dichloromethane for 3 times. Then organic phases were combined and dichloromethane was removed by means of vacuum concentration, to obtain products of 1.5 g of octaethylene glycol

Figure 1:
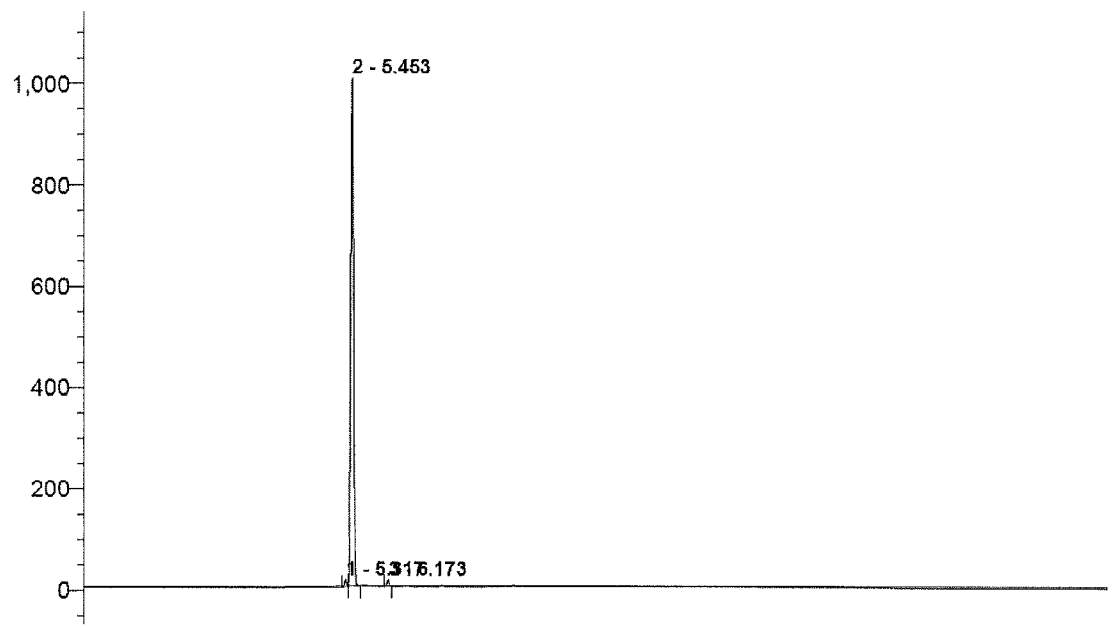
FIG. 1 is a high performance liquid chromatography (HPLC) spectrum of the content of octaethylene glycol (n=7)
Figure 2:
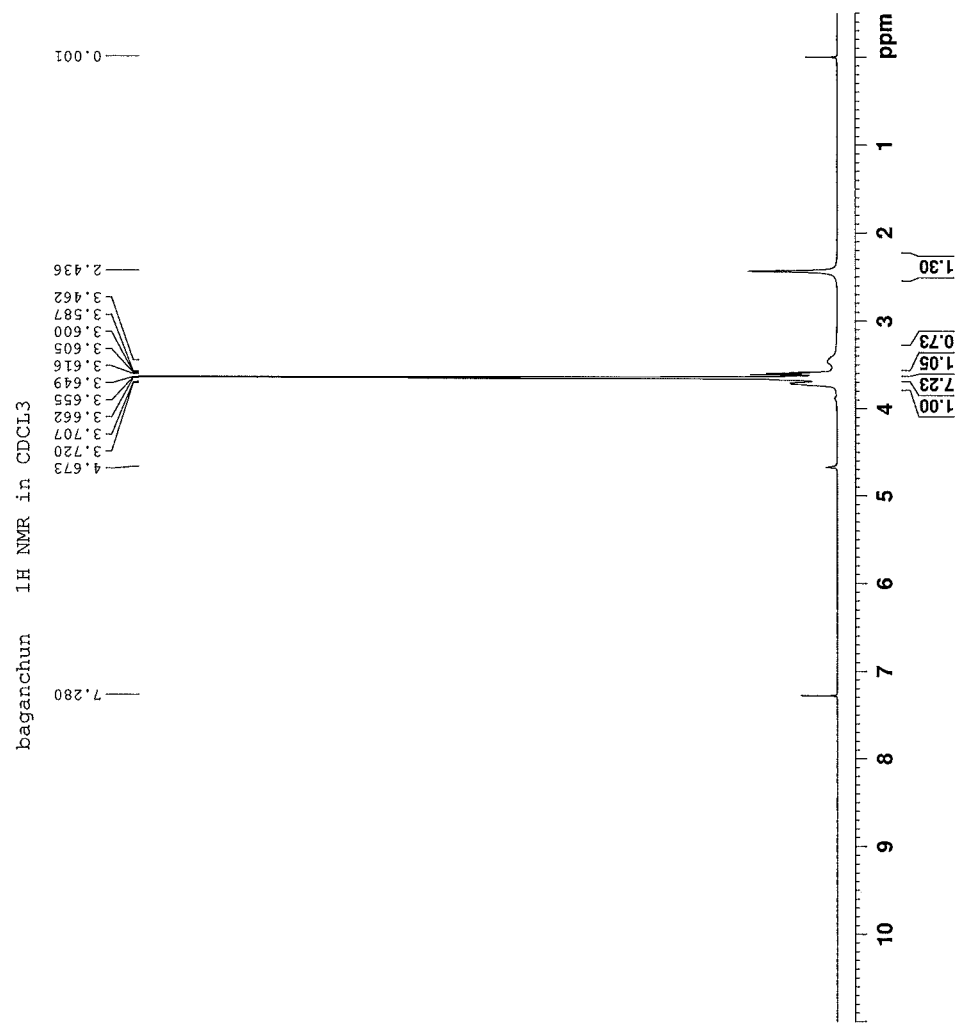
FIG. 2 is a nuclear magnetic resonance spectrum of octaethylene glycol (n=7).

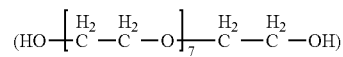

with a polydispersity index of 1.001, a structure determined by nuclear magnetic resonance spectroscopy (as shown in FIG. 2), and a purity detected by high performance liquid chromatography (HPLC) (as shown in FIG. 1) under HPLC detection conditions of a C18 chromatographic column, an evaporative light-scattering detector, and a mobile phase of acetonitrile and water (30:70); and 3.4 g of nonaethylene glycol

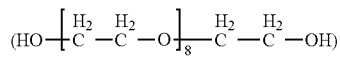

with a polydispersity index of 1.000.

Embodiment 2

50 g (0.25 mol) of polyethylene glycol PEG-200 was taken as a starting material and dissolved in 1,000 ml of tetrahydrofuran. Then, to the resulting solution, 10 g (0.125 mol) of 50% sodium hydroxide solution was added dropwise and further stirred for 2 h. 7 g (0.025 mol) of triphenylmethyl chloride was then added for reaction at a temperature of 20° C. over 12 h. 300 ml of saturated ammonium chloride solution was added into the reaction liquid and stirred for stratification. The organic phase was washed with saturated aqueous solution of sodium chloride to neutral. After the solvent was removed by means of vacuum concentration, a mixed sample of 9.5 g of polyethylene glycol mono(triphenylmethyl) ester and polyethylene glycol bis(triphenylmethyl) ester was obtained. To the above sample, 12 g of silica gel and 50 ml of ethyl acetate were added, evenly dispersed and dried to prepare a silica gel sample. 200 g of silica gel was added into a glass chromatography column with a diameter of 80 mm, and vibrated to become dense. Then, the above silica gel sample and a small amount of anhydrous sodium sulfate were added into the glass chromatography column, to prevent surface disturbance of the silica gel sample. After a silica gel column for chromatography was formed, an eluent (P/E=1:1) was slowly added continuously. Samples of different components were collected according to different polarities, and after the eluent was removed, derivatives of polyethylene glycol with a pure component were obtained. Then, 100 ml of 5% hydrochloric acid solution was separately added into the derivatives of polyethylene glycol, stirred at 50° C. and hydrolyzed for 8 h. After being cooled, the derivatives of polyethylene glycol were separately extracted with 100 ml of dichloromethane for 3 times. Then organic phases were combined and dichloromethane was removed by means of vacuum concentration, to obtain products of 3.7 g of tetraethylene glycol

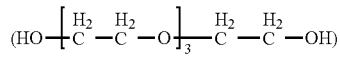

with a polydispersity index of 1.000, and 1.1 g of pentaethylene glycol

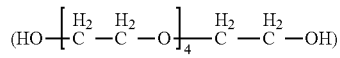

with a polydispersity index of 1.001.

Embodiment 3

300 g (0.50 mol) of polyethylene glycol PEG-600 was taken as a starting material and dissolved in 1,000 ml of tetrahydrofuran. Then, to the resulting solution, 1.8 g (0.075 mol) of sodium hydride solution was added in portions and further stirred for 2 h. 4.6 g (0.025 mol) of 4-methylbenzyl bromide was then added for reaction at a temperature of 0° C. over 72 h. 300 ml of saturated ammonium chloride solution was added into the reaction liquid and stirred for stratification. The organic phase was washed with saturated aqueous solution of sodium chloride to neutral. After the solvent was removed by means of vacuum concentration, a mixed sample of 7.2 g of polyethylene glycol mono(4-methylbenzyl) ester was obtained. To the above sample, 12 g of silica gel and 50 ml of ethyl acetate were added, evenly dispersed and dried to prepare a silica gel sample. 200 g of silica gel was added into a glass chromatography column with a diameter of 80 mm, and vibrated to become dense. Then, the above silica gel sample and a small amount of anhydrous sodium sulfate were added into the glass chromatography column, to prevent surface disturbance of the silica gel sample. After a silica gel column for chromatography was formed, a mixed solvent (D/M=10:1) of dichloromethane and methanol was slowly added as an eluent continuously. Samples of different components were collected according to different polarities, and after the eluent was removed, derivatives of polyethylene glycol with a pure component were obtained. Then, 100 ml of 5% hydrochloric acid solution was separately added into the derivatives of polyethylene glycol, stirred at 50° C. and hydrolyzed for 8 h. After being cooled, the derivatives of polyethylene glycol were separately extracted with 100 ml of dichloromethane for 3 times. Then organic phases were combined and dichloromethane was removed by means of vacuum concentration, to obtain a product of 2.7 g of trideca(ethylene glycol)

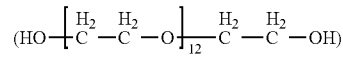

(n=12) with a polydispersity index of 1.002.

Embodiment 4

150 g (0.10 mol) of polyethylene glycol PEG-1500 was taken as a starting material and dissolved in 1,000 ml of tetrahydrofuran. Then, to the resulting solution, 0.46 g (0.02 mol) of sodium metal was added in portions and further stirred for 2 h. 4.8 g (0.025 mol) of 4-methylbenzenesulfonyl chloride was then added for reaction at a temperature of 60° C. over 8 h. 300 ml of saturated ammonium chloride solution was added into the reaction liquid and stirred for stratification. The organic phase was washed with saturated aqueous solution of sodium chloride to neutral. After the solvent was removed by means of vacuum concentration, a mixed sample of 11.2 g of polyethylene glycol p-toluenesulfonate was obtained. To the above sample, 12 g of silica gel and 50 ml of ethyl acetate were added, evenly dispersed and dried to prepare a silica gel sample. 200 g of silica gel was added into a glass chromatography column with a diameter of 80 mm, and vibrated to become dense. Then, the above silica gel sample and a small amount of anhydrous sodium sulfate were added into the glass chromatography column, to prevent surface disturbance of the silica gel sample. After a silica gel column for chromatography was formed, an eluent (P/E=3:1) was slowly added continuously. Samples of different component were collected according to different polarities, and after the eluent was removed, derivatives of polyethylene glycol with a pure component were obtained. Then, 100 ml of 5% sodium hydroxide solution was separately added into the derivatives of polyethylene glycol, stirred at 50° C. and hydrolyzed for 8 h. After being cooled, the derivatives of polyethylene glycol were separately extracted with 100 ml of dichloromethane for 3 times. Then organic phases were combined and dichloromethane was removed by means of vacuum concentration, to obtain a product of 5.3 g of tritriaconta(ethylene glycol)

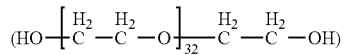

(n=32) with a polydispersity index of 1.004.

Control Example 8 g of starting material of polyethylene glycol PEG-400 was taken as a starting material, to which 12 g of silica gel and 50 ml of ethyl acetate were added, evenly dispersed and dried to prepare a silica gel sample. 200 g of silica gel was added into a glass chromatography column with a diameter of 80 mm, and vibrated to become dense. Then, the above silica gel sample and a small amount of anhydrous sodium sulfate were added into the glass chromatography column, to prevent surface disturbance of the silica gel sample. After a silica gel column for chromatography was formed, an eluent (a mixed solvent of ethyl acetate and petroleum ether with a volume ratio of 1:1) was slowly added. Then, samples were collected and analyzed. The product was still a mixture of polyethylene glycols, and had not been separated. For the starting material, products and polydispersity index in Embodiment 1 to Embodiment 4, refer to Table 1.

2. The process for preparing and separating a monodisperse polyethylene glycol according to claim 1, wherein the starting material of polyethylene glycol has general formula of:

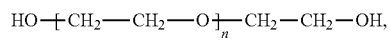

wherein:

n=3 to 50, and a polydispersity index thereof is greater than 1.1; and the derivatives of polyethylene glycol with different polarities have general formula of:

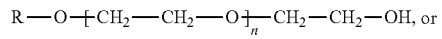
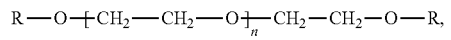

wherein:

n=3 to 50.

3. The process for preparing and separating a monodisperse polyethylene glycol according to claim 1, wherein the monodisperse polyethylene glycol has a polydispersity index of 1 to 1.03.

4. The process for preparing and separating a monodisperse polyethylene glycol according to claim 1, wherein the

TABLE 1

Starting Material, Products and Polydispersity Index in Embodiment 1 to Embodiment 4

| | Starting material | Molecular weight distribution | Polydispersity index | R-B | Eluent | n | Polydispersity index |
|---|---|---|---|---|---|---|---|
| Embodiment 1 | PEG-400 | 380-420 | 1.15 | Isobutyl chloride | P/E = 1:1 | 7 | 1.001 |
| | | | | | | 8 | 1.000 |
| Embodiment 2 | PEG-200 | 180-220 | 1.12 | Triphenylmethyl chloride | P/E = 1:1 | 3 | 1.000 |
| | | | | | | 4 | 1.001 |
| Embodiment 3 | PEG-600 | 540-660 | 1.27 | 4-methylbenzyl bromide | D/M = 10:1 | 1 | 1.002 |
| | | | | | | 2 | |
| Embodiment 4 | PEG-1500 | 1350-1650 | 1.32 | 4-methylbenzenesulfonyl chloride | P/E = 3:1 | 3 | 1.004 |
| | | | | | | 2 | |

What is claimed is:

1. A process for preparing and separating a monodisperse polyethylene glycol, comprising:
   reacting a starting material of polyethylene glycol dissolved into an organic solvent with a compound represented by general formula I under catalytic action of an alkaline substance, to prepare a mixture of derivatives of polyethylene glycol having different polarities;
   separating the mixture of the derivatives of polyethylene glycol by means of silica gel column chromatography, to obtain a monodisperse derivative of polyethylene glycol; and
   hydrolyzing the monodisperse derivative of polyethylene glycol to obtain a monodisperse polyethylene glycol,
   wherein, general formula I is as follows:
   R—B,
   where:
   R is a $C_1$-$C_4$ alkyl or an aryl; and
   B is selected from the group consisting of a chloride ion, a bromide ion, an iodide ion, sulfydryl, sulfonyl, an isocyanate group, and an isocyanurate group.

$C_1$-$C_4$ alkyl is selected from the group consisting of methyl, ethyl, n-propyl, isopropyl, 1-butyl, 2-butyl, and isobutyl; and the aryl is selected from the group consisting of phenyl, 2-methylphenyl, 4-methylphenyl, benzyl, 2-methylbenzyl, 4-methylbenzyl, 4-tosyl, and triphenylmethyl.

5. The process for preparing and separating a monodisperse polyethylene glycol according to claim 1, wherein a molar ratio of the starting material of polyethylene glycol to the compound represented by general formula I is 2:1 to 100:1, and a molar ratio of the starting material of polyethylene glycol to the alkaline substance is 1:1 to 20:1.

6. The process for preparing and separating a monodisperse polyethylene glycol according to claim 5, wherein the molar ratio of the starting material of polyethylene glycol to the compound represented by general formula I is 4:1 to 20:1, and the molar ratio of the starting material of polyethylene glycol to the alkaline substance is 2:1 to 7:1.

7. The process for preparing and separating a monodisperse polyethylene glycol according to claim 1, wherein a reaction temperature for the reaction of the starting material of polyethylene glycol with the compound represented by general formula I is −20° C. to 150° C., and a reaction duration thereof is 3 h to 72 h.

8. The process for preparing and separating a monodisperse polyethylene glycol according to claim 7, wherein the reaction temperature for the reaction of the starting material of polyethylene glycol with the compound represented by general formula I is 0° C. to 60° C., the reaction duration is 8 h to 72 h.

9. The process for preparing and separating a monodisperse polyethylene glycol according to claim 1, wherein
the organic solvent is at least one selected from the group consisting of dichloromethane, trichloromethane, benzene, toluene, dimethylformamide, dimethyl sulfoxide, tetrahydrofuran and 1,4-dioxane;
the alkaline substance is at least one selected from the group consisting of an alkali metal, an alkaline-earth metal, and a corresponding oxide, hydroxide, and hydride thereof; and
the eluent during the process of silica gel column chromatography is a mixture of two selected from the group consisting of formamide, acetonitrile, methanol, ethanol, propyl alcohol, acetone, dioxane, tetrahydrofuran, methyl ethyl ketone, n-butanol, ethyl acetate, diethyl ether, isopropyl ether, dichloromethane, chloroform, benzene, tetrachloromethane, carbon disulfide, cyclohexane, n-hexane and petroleum ether.

10. The process for preparing and separating a monodisperse polyethylene glycol according to claim 9, wherein
the organic solvent is tetrahydrofuran or 1,4-dioxane;
the alkaline substance is sodium metal, sodium hydroxide or sodium hydride; and
the eluent during the process of silica gel column chromatography is a mixed solvent of ethyl acetate and petroleum ether, or a mixed solvent of dichloromethane and methanol.

11. The process for preparing and separating a monodisperse polyethylene glycol according to claim 1, wherein the monodisperse polyethylene glycol has a polydispersity index of 1 to 1.005.

12. A process for obtaining a monodisperse polyethylene glycol, comprising:
reacting a starting material of polyethylene glycol having a polydispersity index greater than 1.1 that is dissolved into an organic solvent with a compound represented by general formula I under catalytic action of an alkaline substance, to prepare a mixture of derivatives of polyethylene glycol having different polarities;
separating the mixture of the derivatives of polyethylene glycol by means of silica gel column chromatography, to obtain a monodisperse derivative of polyethylene glycol; and
hydrolyzing the monodisperse derivative of polyethylene glycol to obtain a monodisperse polyethylene glycol having a polydispersity index of 1 to 1.03,
wherein, general formula I is as follows:

R—B, where:
R is a $C_1$-$C_4$ alkyl or an aryl; and
B is selected from the group consisting of a chloride ion, a bromide ion, an iodide ion, sulfydryl, sulfonyl, an isocyanate group, and an isocyanurate group.

13. The process for obtaining a monodisperse polyethylene glycol according to claim 12, wherein the monodisperse polyethylene glycol has a polydispersity index of 1 to 1.005.

* * * * *